United States Patent
Ishikawa et al.

(10) Patent No.: US 8,536,302 B2
(45) Date of Patent: Sep. 17, 2013

(54) DOCKERIN POLYPEPTIDE AND METHOD OF PURIFYING RECOMBINANT FUSED PROTEIN USING THE SAME

(75) Inventors: Yukiko Ishikawa, Sayama (JP); Yoshiko Kamezaki, Sayama (JP); Chiaki Enomoto, Sayama (JP)

(73) Assignee: Sysmex Corporation, Hyogo (JP)

( * ) Notice: Subject to any disclaimer, the term of this patent is extended or adjusted under 35 U.S.C. 154(b) by 402 days.

(21) Appl. No.: 12/675,316

(22) PCT Filed: Aug. 27, 2008

(86) PCT No.: PCT/JP2008/065261
§ 371 (c)(1),
(2), (4) Date: Feb. 25, 2010

(87) PCT Pub. No.: WO2009/028531
PCT Pub. Date: Mar. 5, 2009

(65) Prior Publication Data
US 2010/0204445 A1   Aug. 12, 2010

(30) Foreign Application Priority Data

Aug. 27, 2007 (JP) ................................ 2007-219362
Dec. 13, 2007 (JP) ................................ 2007-321497

(51) Int. Cl.
*A61K 38/00* (2006.01)

(52) U.S. Cl.
USPC ........................................................ 530/324

(58) Field of Classification Search
None
See application file for complete search history.

(56) References Cited

U.S. PATENT DOCUMENTS
2005/0106700 A1   5/2005 Nomura et al.

FOREIGN PATENT DOCUMENTS
JP    7 184663    7/1995
JP    2686090     8/1997
WO    03 033695   4/2003

OTHER PUBLICATIONS

Jindou, Sadanari. et al., "Cohesin-Dockerin Interactions within and between *Clostridium josui* and *Clostridium thermocellum*, Binding Selectivity Between Cognate Dockerin and Cohesin Domains and Species Specificity", The Journal of Biological Chemistry, vol. 279, No. 11, pp. 9867-9874, (2004).

Miras, Isabelle et al., "Mapping by Site-Directed Mutagenesis of the Region Responsible for Cohesin-Dockerin Interaction on the Surface of the Seventh Cohesin Domain of *Clostridium thermocellum* CipA", Biochemistry, vol. 41, No. 7, pp. 2115-2119, (2002).

Craig, Scott J. et al., "Engineered proteins containing the cohesion and dockerin domains from *Clostridium thermocellum* provides a reversible, high affinity interaction for biotechnology applications", Journal of Biotechnology, vol. 121, pp. 165-173, (2006).

Karita, Shuichi et al., "Features of Cellulases Elucidated by Molecular Biological Approaches", The Bulletin of the Faculty of Bioresources, vol. 19, pp. 71 to 96, (1997), (with English abstract).

*Primary Examiner* — Mark Navarro
*Assistant Examiner* — Khatol Shahnan-Shah
(74) *Attorney, Agent, or Firm* — Oblon, Spivak, McClelland, Maier & Neustadt, L.L.P.

(57) ABSTRACT

The purpose of the invention is to provide a novel purification system allowing the efficient and economical production and purification of a recombinant fused protein, whereby the elution time at a low temperature can be reduced, since it has been a problem to be solved in the existing purification method using dockerin and cohesin. In this purification system, a dockerin polypeptide characterized in that the 14th amino acid in the subdomain 2 of dockerin originating from *Clostridium josui* is substituted with another amino acid, and a method for purification of a recombinant fused protein are provided.

13 Claims, 7 Drawing Sheets

Fig. 1 pM0NDT10
1  MGLKGDVNNDGAIDALDIAALKKAILTQSTSNINLTNADMNNDGNIDAIDFAQLKVKLLN  60 pM0NDT10-DV(I49T)
1  MGLKGDVNNDGAIDALDIAALKKAILTQSTSNINLTNADMNNDGNIDA[T]DFAQLKVKLLN  60 pM0NDT10-DV(I49G)
1  MGLKGDVNNDGAIDALDIAALKKAILTQSTSNINLTNADMNNDGNIDA[G]DFAQLKVKLLN  60 pM0NDT10-DV(I49S)
1  MGLKGDVNNDGAIDALDIAALKKAILTQSTSNINLTNADMNNDGNIDA[S]DFAQLKVKLLN  60 pM0NDT10-DV(I49N)
1  MGLKGDVNNDGAIDALDIAALKKAILTQSTSNINLTNADMNNDGNIDA[N]DFAQLKVKLLN  60 pM0NDT10-DV(L16T, I49T)
1  MGLKGDVNNDGAIDA[T]DIAALKKAILTQSTSNINLTNADMNNDGNIDA[T]DFAQLKVKLLN  60 pM0NDT10-DV(I49Y)
1  MGLKGDVNNDGAIDALDIAALKKAILTQSTSNINLTNADMNNDGNIDA[Y]DFAQLKVKLLN  60 pM0NDT10-DV(L16G, I49G)
1  MGLKGDVNNDGAIDA[G]DIAALKKAILTQSTSNINLTNADMNNDGNIDA[G]DFAQLKVKLLN  60 pM0NDT10-DV(I49V)
1  MGLKGDVNNDGAIDALDIAALKKAILTQSTSNINLTNADMNNDGNIDA[V]DFAQLKVKLLN  60 pM0CDT17

1  MGLKGDVNNDGAIDALDIAALKKAILTQSTSNINLTNADMNNDGNIDAIDFAQLKVKLLN  60 pM0CDT17-DV(I49T)

1  MGLKGDVNNDGAIDALDIAALKKAILTQSTSNINLTNADMNNDGNIDA[T]DFAQLKVKLLN  60 pM0CDT17-DV(L16T, I49T)

1  MGLKGDVNNDGAIDA[T]IAALKKAILTQSTSNINLTNADMNNDGNIDA[T]DFAQLKVKLLN  60

Fig. 5
(A)
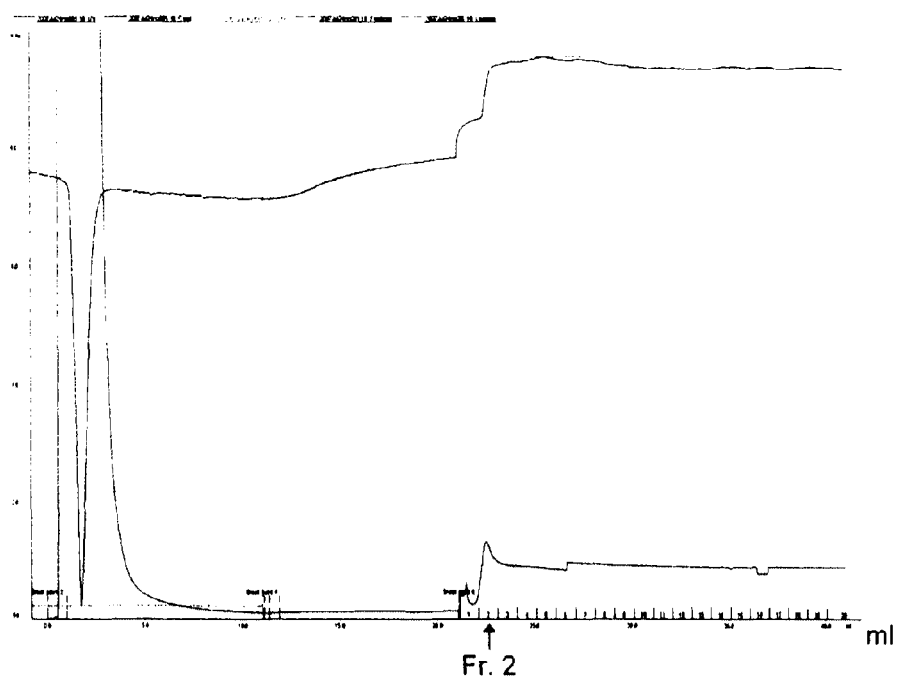
Fr. 2
(B)
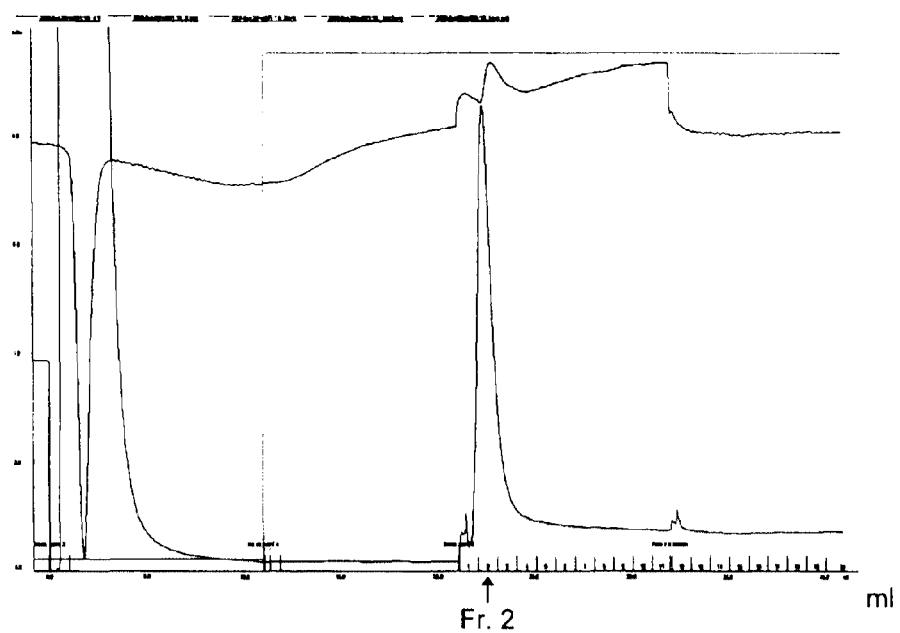
Fr. 2

Fig. 6
(A)
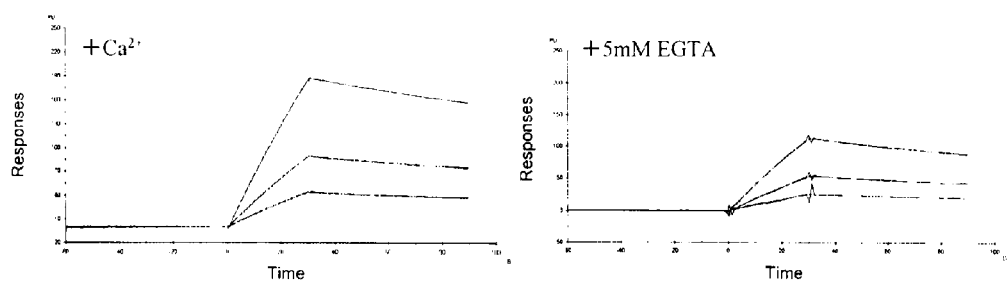
(B)
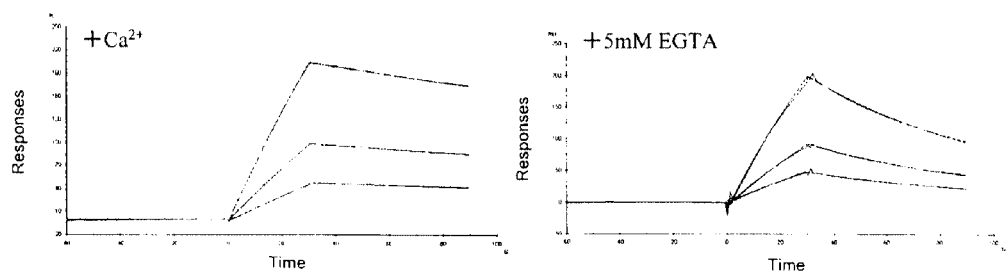
(C)
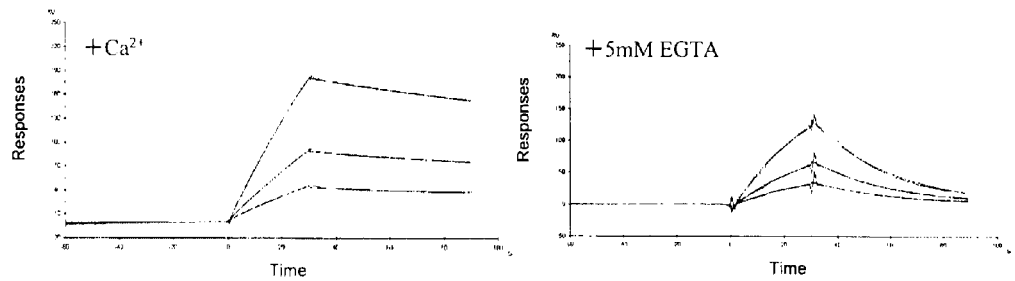

Fig. 7
(A)
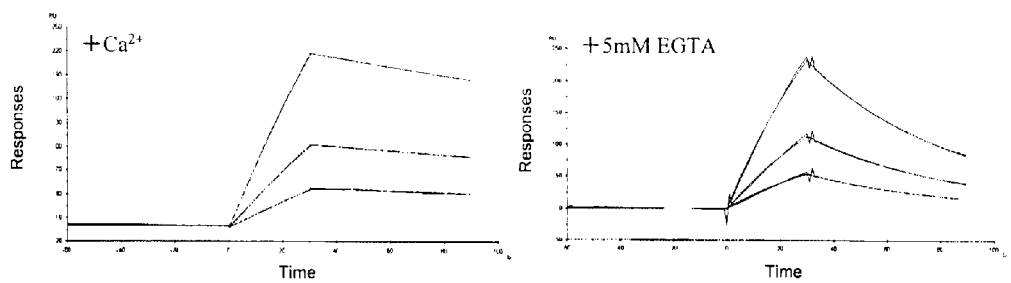
(B)
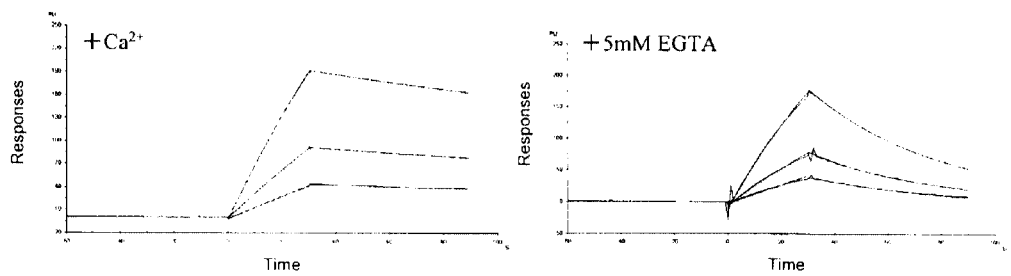
(C)
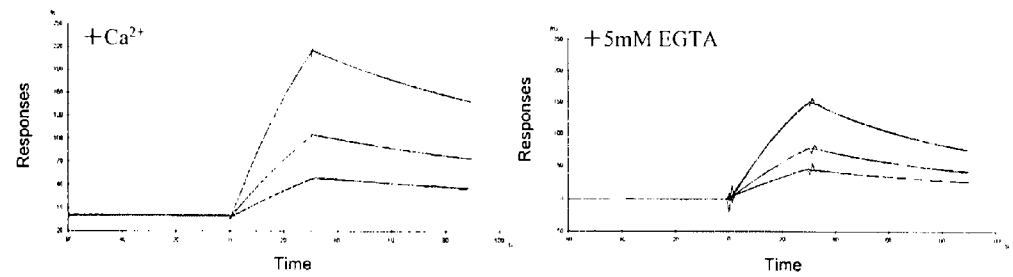

SEQUENCE LISTING

<160> NUMBER OF SEQ ID NOS: 11

<210> SEQ ID NO 1
<211> LENGTH: 60
<212> TYPE: PRT
<213> ORGANISM: Clostridium josui

<400> SEQUENCE: 1

Met Gly Leu Lys Gly Asp Val Asn Asn Asp Gly Ala Ile Asp Ala Leu
1               5                   10                  15

Asp Ile Ala Ala Leu Lys Lys Ala Ile Leu Thr Gln Ser Thr Ser Asn
            20                  25                  30

Ile Asn Leu Thr Asn Ala Asp Met Asn Asp Gly Asn Ile Asp Ala
        35                  40                  45

Ile Asp Phe Ala Gln Leu Lys Val Lys Leu Leu Asn
    50                  55                  60

<210> SEQ ID NO 2
<211> LENGTH: 77
<212> TYPE: PRT
<213> ORGANISM: Clostridium josui

<400> SEQUENCE: 2

Ile Glu Phe Gly Asp Val Asp Gly Asn Gly Met Ile Asp Ala Leu Asp
1               5                   10                  15

Tyr Ser Leu Val Lys Arg Tyr Leu Leu Gly Gln Ile Ser Asp Cys Pro
            20                  25                  30

Asp Ser Lys Gly Lys Leu Ala Ala Asp Val Asp Gly Asp Gln Gln Ile
            35                  40                  45

Thr Ala Leu Asp Phe Ser Leu Ile Lys Gln Tyr Leu Leu Gly Thr Ile
        50                  55                  60

Asn Lys Phe Pro Ala Gln Thr Ala Ser Lys Ile Lys Pro
65                  70                  75

<210> SEQ ID NO 3
<211> LENGTH: 60
<212> TYPE: PRT
<213> ORGANISM: Clostridium josui

<400> SEQUENCE: 3

Ser Asn Leu Gly Asp Val Asn Gly Asp Glu Thr Val Asp Ala Ile Asp
1               5                   10                  15

Leu Ala Met Leu Lys Lys Tyr Leu Leu Asn Ser Ser Thr Ser Ile Val
            20                  25                  30

Ala Gly Asn Ala Asp Met Asn Gly Asp Gly Ala Ile Asp Ala Ile Asp
        35                  40                  45

Tyr Ala Leu Leu Lys Lys Ala Leu Leu Ala Asn Gln
    50                  55                  60

<210> SEQ ID NO 4
<211> LENGTH: 60
<212> TYPE: PRT
<213> ORGANISM: Artificial
<220> FEATURE:
<223> OTHER INFORMATION: I49Tsubstituted dockerin

<400> SEQUENCE: 4

Met Gly Leu Lys Gly Asp Val Asn Asn Asp Gly Ala Ile Asp Ala Leu
1               5                   10                  15

-continued

Asp Ile Ala Ala Leu Lys Lys Ala Ile Leu Thr Gln Ser Thr Ser Asn
            20                  25                  30

Ile Asn Leu Thr Asn Ala Asp Met Asn Asn Asp Gly Asn Ile Asp Ala
            35                  40                  45

Thr Asp Phe Ala Gln Leu Lys Val Lys Leu Leu Asn
    50                  55                  60

<210> SEQ ID NO 5
<211> LENGTH: 60
<212> TYPE: PRT
<213> ORGANISM: Artificial
<220> FEATURE:
<223> OTHER INFORMATION: I49Gsubstituted dockerin

<400> SEQUENCE: 5

Met Gly Leu Lys Gly Asp Val Asn Asn Asp Gly Ala Ile Asp Ala Leu
1               5                   10                  15

Asp Ile Ala Ala Leu Lys Lys Ala Ile Leu Thr Gln Ser Thr Ser Asn
            20                  25                  30

Ile Asn Leu Thr Asn Ala Asp Met Asn Asn Asp Gly Asn Ile Asp Ala
            35                  40                  45

Gly Asp Phe Ala Gln Leu Lys Val Lys Leu Leu Asn
    50                  55                  60

<210> SEQ ID NO 6
<211> LENGTH: 60
<212> TYPE: PRT
<213> ORGANISM: Artificial
<220> FEATURE:
<223> OTHER INFORMATION: I49Ssubstituted dockerin

<400> SEQUENCE: 6

Met Gly Leu Lys Gly Asp Val Asn Asn Asp Gly Ala Ile Asp Ala Leu
1               5                   10                  15

Asp Ile Ala Ala Leu Lys Lys Ala Ile Leu Thr Gln Ser Thr Ser Asn
            20                  25                  30

Ile Asn Leu Thr Asn Ala Asp Met Asn Asn Asp Gly Asn Ile Asp Ala
            35                  40                  45

Ser Asp Phe Ala Gln Leu Lys Val Lys Leu Leu Asn
    50                  55                  60

<210> SEQ ID NO 7
<211> LENGTH: 60
<212> TYPE: PRT
<213> ORGANISM: Artificial
<220> FEATURE:
<223> OTHER INFORMATION: I49Nsubstituted dockerin

<400> SEQUENCE: 7

Met Gly Leu Lys Gly Asp Val Asn Asn Asp Gly Ala Ile Asp Ala Leu
1               5                   10                  15

Asp Ile Ala Ala Leu Lys Lys Ala Ile Leu Thr Gln Ser Thr Ser Asn
            20                  25                  30

Ile Asn Leu Thr Asn Ala Asp Met Asn Asn Asp Gly Asn Ile Asp Ala
            35                  40                  45

Asn Asp Phe Ala Gln Leu Lys Val Lys Leu Leu Asn
    50                  55                  60

<210> SEQ ID NO 8
<211> LENGTH: 60
<212> TYPE: PRT
<213> ORGANISM: Artificial

<220> FEATURE:
<223> OTHER INFORMATION: L16T, I49Tsubstituted dockerin

<400> SEQUENCE: 8

```
Met Gly Leu Lys Gly Asp Val Asn Asn Asp Gly Ala Ile Asp Ala Thr
1               5                   10                  15

Asp Ile Ala Ala Leu Lys Lys Ala Ile Leu Thr Gln Ser Thr Ser Asn
            20                  25                  30

Ile Asn Leu Thr Asn Ala Asp Met Asn Asn Asp Gly Asn Ile Asp Ala
        35                  40                  45

Thr Asp Phe Ala Gln Leu Lys Val Lys Leu Leu Asn
    50                  55                  60
```

<210> SEQ ID NO 9
<211> LENGTH: 60
<212> TYPE: PRT
<213> ORGANISM: Artificial
<220> FEATURE:
<223> OTHER INFORMATION: I49Ysubstituted dockerin

<400> SEQUENCE: 9

```
Met Gly Leu Lys Gly Asp Val Asn Asn Asp Gly Ala Ile Asp Ala Leu
1               5                   10                  15

Asp Ile Ala Ala Leu Lys Lys Ala Ile Leu Thr Gln Ser Thr Ser Asn
            20                  25                  30

Ile Asn Leu Thr Asn Ala Asp Met Asn Asn Asp Gly Asn Ile Asp Ala
        35                  40                  45

Tyr Asp Phe Ala Gln Leu Lys Val Lys Leu Leu Asn
    50                  55                  60
```

<210> SEQ ID NO 10
<211> LENGTH: 60
<212> TYPE: PRT
<213> ORGANISM: Artificial
<220> FEATURE:
<223> OTHER INFORMATION: L16G, I49Gsubstituted dockerin

<400> SEQUENCE: 10

```
Met Gly Leu Lys Gly Asp Val Asn Asn Asp Gly Ala Ile Asp Ala Gly
1               5                   10                  15

Asp Ile Ala Ala Leu Lys Lys Ala Ile Leu Thr Gln Ser Thr Ser Asn
            20                  25                  30

Ile Asn Leu Thr Asn Ala Asp Met Asn Asn Asp Gly Asn Ile Asp Ala
        35                  40                  45

Gly Asp Phe Ala Gln Leu Lys Val Lys Leu Leu Asn
    50                  55                  60
```

<210> SEQ ID NO 11
<211> LENGTH: 60
<212> TYPE: PRT
<213> ORGANISM: Artificial
<220> FEATURE:
<223> OTHER INFORMATION: I49Vsubstituted dockerin

<400> SEQUENCE: 11

```
Met Gly Leu Lys Gly Asp Val Asn Asn Asp Gly Ala Ile Asp Ala Leu
1               5                   10                  15

Asp Ile Ala Ala Leu Lys Lys Ala Ile Leu Thr Gln Ser Thr Ser Asn
            20                  25                  30

Ile Asn Leu Thr Asn Ala Asp Met Asn Asn Asp Gly Asn Ile Asp Ala
        35                  40                  45
```

-continued

```
Val Asp Phe Ala Gln Leu Lys Val Lys Leu Leu Asn
 50              55                  60
```

DOCKERIN POLYPEPTIDE AND METHOD OF PURIFYING RECOMBINANT FUSED PROTEIN USING THE SAME

TECHNICAL FIELD

The present invention relates to a novel polypeptide which can be utilized in purification and so on of recombinant fused proteins in a short period of time and to a method for purifying a recombinant fused protein utilizing the same.

BACKGROUND ART

Since the genomic analysis has been completed and all of the expressed genes are being elucidated, the importance of the functional analysis of proteins has increased. In addition, owing to the development of molecular biology, it has become possible to make a large quantity of proteins express as recombinant proteins by means of introducing recombinant genes into the cells of animals and plants, yeasts, bacteria, and the like, in place of purification of proteins from living tissues.

In order to obtain a recombinant protein, however, it is necessary to separate and purify an aimed recombinant protein from a large quantity of cell-derived impurities such as proteins, nucleic acids, polysaccharides and so on, after expression of the recombinant protein and homogenate of the cells in a general way. In the production of recombinant proteins using cells as host, accordingly, it is a very important issue for the functional analysis and utilization of proteins to carry out the separation and purification of an aimed recombinant protein efficiently.

A frequently-used effective method for separating and purifying recombinant proteins is affinity chromatography. In this method, a gene sequence coding for the aimed protein and another gene sequence coding for a protein fragment having a high affinity to a certain ligand (hereinafter, referred to as affinity peptide) are utilized to make express a recombinant fused protein in which the aimed protein is combined with the affinity peptide. Subsequently, this recombinant fused protein is isolated from other impurities by using a carrier on which the ligand binding to the fused affinity peptide has been immobilized, and then the affinity peptide is dissociated therefrom. Thus, the aimed peptide can conveniently be purified. In practice, there are some procedures known as affinity chromatography, i.e., procedure using polyhistidine (Patent document 1), procedure using glutathione-S-transferase (GST) (Patent document 2), and procedure utilizing a maltose-binding protein (MBP).

However, there were some problems in most of the affinity chromatography which had been developed in the past. For example, some recombinant fused proteins having a combination of polyhistidine and an aimed protein were often insolublized by a host or did not show an inherent activity. In particular, when a huge affinity peptide having the molecular weight of about 30-50 kDa such as GST or MBP was fused, they were sometimes expressed as a recombinant fused protein having no inherent activity because their normal folding was obstructed. Further, there was an economic problem since a highly expensive ligand such as IgG antibody had to be used as a carrier for affinity chromatography. Additionally, for some affinity peptides, the recombinant fused proteins had to be eluted from the carrier at a pH value which may inactivate the aimed protein, or it was necessary to add a substance such as guanidine or ethylene glycol, which worked to denature the aimed protein or inhibit the activity. That is, affinity chromatography may have a practical problem that dissociation was difficult under a mild condition, though it enables highly specific purification by utilizing an fused affinity peptide and a ligand corresponding thereto.

In view of this situation, the present inventors have reported that a recombinant fused protein can be separated and purified in a relatively mild condition by utilizing dockerin, a protein which is a part of a protein complex termed cellulosome originating from *Clostridium josui* (reported by Ohmiya et al. in Non-patent document 1) and containing a calcium-binding motif domain, and another protein cohesin domain specifically binding via calcium ion (Patent document 3).

In this method for purification, however, there is a problem that when the recombinant fused protein is eluted at a low temperature around 4° C. in order to suppress denaturation of the protein, it takes 6 to 16 hours to elute the protein because the binding of dockerin to cohesin domain is strong. On the other hand, the protein can be eluted within a short period of time at ordinary temperature, but in such a case, there is concern that the activity of protein might be affected.

Patent document 1: Japanese Patent No. 2686090
Patent document 2: JP-A-H07-184663A
Patent document 3: WO 03/033695 International Publication Pamphlet
Non-patent document 1: The bulletin of the Faculty of Bioresource, Mie University, No. 19, pp 71-96 (1997)

DISCLOSURE OF INVENTION

Problem to be Solved by the Invention

Thus, there has been a demand to develop a novel purification system allowing the efficient and economical production and purification of a recombinant fused protein, by reducing the elution time at a low temperature, which is a problem in the existing purification method using dockerin and cohesin. The purpose of the invention is to provide such a purification system.

Means for Solving the Problems

The present inventors worked assiduously to solve the above-mentioned problems and found that the time for elution of the aimed protein is markedly reduced even at a low temperature. Thus, the invention was completed by using a dockerin polypeptide which is obtained by replacing an amino acid located at a certain position of the amino acid sequence of dockerin with another certain amino acid in a conventional purification method using dockerin and cohesin.

Namely, the present invention provides a dockerin polypeptide which is characterized in that the 14th amino acid isoleucine or leucine in the subdomain 2 of dockerin originating from *Clostridium josui* is substituted with another certain amino acid selected from the group consisting of threonine, glycine, serine, tyrosine and aspargine.

In addition, the present invention provides a method for purification of a recombinant fused protein which comprises forming a complex by binding a recombinant fused protein constituted by an aimed protein and the above-mentioned dockerin polypeptide to a polypeptide containing cohesin domain via calcium ion, then removing the calcium ion from the complex with a metal chelating agent, and eluting the recombinant fused protein.

Further, the present invention provides a polynucleotide coding for the above-mentioned dockerin peptide and an expression vector integrated with the same.

Furthermore, the present invention provides a kit for purification of recombinant fused proteins, characterized by containing the above-mentioned expression vector and a carrier on which a polypeptide containing cohesin domain is immobilized.

Effects of the Invention

The dockerin polypeptide of the present invention has the same binding affinity to cohesin domain as the wild-type dockerin. And when this is applied in purification of a recombinant fused protein using a known wild-type dockerin and cohesin, it is possible to reduce the elution time at a low temperature at which the activity of recombinant fused proteins is scarcely affected.

Thus, the method of the present invention for purifying a recombinant fused protein utilizing a dockerin polypeptide can be used efficiently and economically in purification of recombinant fused proteins.

BEST MODE FOR CARRYING OUT THE INVENTION

In this description, the dockerin originating from *Clostridium josui* is contained in the cellulosome such as CelB, Aga27A, Cel48A, and the like, which are produced by *Clostridium josui*. For example, the dockerin contained in CelB is located on the 402nd-460th position of the amino acid sequence (BAA04078 or P37701) of CelB (SEQ ID NO: 1), that contained in Aga27A on the 402nd-478th position of the amino acid sequence (BAB83765) of Aga27A (SEQ ID NO: 2), and that contained in Cel48A on the 660th-719th position of the amino acid sequence (BAA32430) of Cel48A (SEQ ID NO: 3).

The above-mentioned amino acid sequences contain commonly two subdomains, dockerin subdomain 1 and subdomain 2. For example, the subdomain 1 of dockerin contained in CelB is located within the range of the 3rd-27th amino acids in SEQ ID NO: 1, and the subdomain 2 is located within the range of the 36th-60th amino acids. The dockerin subdomain 1 contained in Aga27A is located within the range of the 2nd-26th amino acids in SEQ ID NO: 2, and the subdomain 2 is located within the range of 38th-62nd amino acids. Further, the dockerin subdomain 1 contained in Cel48A is located within the range of 2nd-26th amino acids in SEQ ID NO: 3, and the subdomain 2 within the 34th-53rd amino acids. In these subdomains 1 and 2, there are amino acids binding to calcium (calcium-binding amino acids) at the 4th, 6th, 8th, 12th and 15th amino acids from the first amino acid, which form calcium-binding sites.

The dockerin polypeptide of the present invention can be prepared by substituting the 14th amino acid, isoleucine or leucine, of the subdomain 2 (amino acid just before the calcium-binding amino acid at lowest downstream side of subdomain 2) of dockerin originating from the above-mentioned *Clostridium josui* with another certain amino acid selected from the group consisting of threonine, glycine, serine, tyrosine and asparagine. By the substitution with these particular amino acids, it becomes possible to markedly reduce the elution time of purified proteins from the cohesin-immobilized carrier (90% or more eluted within 30 minutes) at a low temperature with acceleration of the rate of dissociation from cohesin only under action of a chelating agent, without changing the binding affinity to cohesin in the presence of calcium ion. On the other hand, when an amino acid other than the above-specified amino acids, for example, valine, is used in the substitution, there is no change in the rate of dissociation from cohesin under action of a chelating agent, and remarkable reduction of the elution time at a low temperature is not observed.

Among the above-specified amino acids, threonine and glycine are preferred, and glycine is particularly preferred. The substitution with these amino acids more markedly increases the rate of dissociation from cohesin, occurring only under action of a chelating agent; thus, the elution time at a low temperature can be reduced, the elution peak in purification on a column becomes sharp, and a highly concentrated pure protein can be obtained within a short period of time.

In the present invention, in addition to the substitution of the 14th amino acid, isoleucine or leucine, of the above-mentioned subdomain 2 with a certain other amino acid, it is also appropriate to substitute the 14th amino acid, leucine or isoleucine, of the subdomain 1 with a certain other amino acid selected from the group consisting of threonine and glycine.

Preferred examples of the above-mentioned dockerin polypeptide include those in which the 49th wild-type amino acid, isoleucine, from the first amino acid, methionine of the dockerin amino acid sequence (SEQ ID NO: 1) contained in CelB is substituted with threonine (SEQ ID NO: 4), substituted with glycine (SEQ ID NO: 5), substituted with serine (SEQ ID NO: 6), substituted with asparagine (SEQ ID NO: 7) or substituted with tyrosine (SEQ ID NO: 9); those in which the 16th wild-type amino acid, leucine (L), and the 49th wild-type amino acid, isoleucine, from the first amino acid, methionine are respectively substituted with threonine (SEQ ID NO: 8); and those in which the 16th wild-type amino acid, leucine (L), and the 49th wild-type amino acid, isoleucine, from the first amino acid, methionine are respectively substituted with glycine (SEQ ID NO: 10). Among these dockerin polypeptides, those in which the 49th wild-type amino acid, isoleucine, from the first amino acid, methionine is substituted with glycine (SEQ ID NO: 5) are particularly preferred.

The dockerin polypeptides of the present invention may be prepared according to a known method by substituting an amino acid with another amino acid for forming a peptide. For example, it is possible to obtain a polynucleotide coding for dockerin polypeptides in which the amino acid just before the last amino acid forming a calcium binding site contained in the wild-type dockerin subdomain is substituted with a desired amino acid, based on a dockerin gene sequence originating from *Clostridium josui*, according to an overlapping extension method (Mikaelian, et al., Nucl. Acids Res., 20, 376 (1992)) by which a mutation can be introduced into the nucleotide, wherein two PCR products containing an overlapping sequence are hybridized and the extended reaction product is used as a secondary PCR template. This polynucleotide can be integrated into an expression vector, which is then introduced into an optional host and the host is incubated to yield the dockerin polypeptide of the invention.

The dockerin polypeptides prepared as mentioned above in the present invention can be utilized in a method for purification of the aimed proteins (hereinafter referred to as "the purification method of the invention") using a polypeptide containing cohesin domain (hereinafter referred to as "cohesin polypeptide"). Specifically, a base sequence which contains a polynucleotide coding for the dockerin polypeptide of the invention and a polynucleotide coding for the aimed protein, is integrated into a proper expression vector and then incubated in a proper host. The resulting recombinant fused protein is associated with cohesin polypeptide via calcium ion to form a complex, from which is then removed the calcium ion with a metal chelating agent, and then the recombinant fused protein is eluted in a purified state. In this connection, the purification method can be carried out according to a method as described in International Patent Publication WO 03/033695 pamphlet.

The recombinant fused protein for use in the purification method of the invention may be obtained by integrating a polynucleotide coding for the dockerin polypeptide of the invention into the upper stream of 5'-range or the down stream of 3'-range of the gene of the aimed protein and then into the down stream of the promoter of an optional expression vector, in the preparation of an expression vector of the above-mentioned dockerin polypeptide of the invention. In this connection, a breakage gene such as thrombin breakage sequence or enterokinase breakage sequence may be introduced between a polynucleotide coding for the dockerin polypeptide of the invention and the gene of the aimed protein. As for the gene of the aimed protein, any genes coding for a variety of known proteins may be used.

The expression vector for use in preparation of the above-mentioned recombinant fused protein is not particularly limited, and the vector may be selected properly according to the host to be employed. For example, when *Escherichia coli* is used as a host, pET (product of Novagen) is used; when insect cultured cells or insect body is used, an expression vector originating from baculovirus such as ABv (Katakura Industires, Co., Ltd.) is preferred; particularly, when an insect body is used, it is preferable to use ABv.

The cohesin polypeptide for use in the purification method of the invention is not particularly limited as far as it binds specifically to the above-mentioned dockerin polypeptide. Such cohesin polypeptides include those originating from *Clostridium josui*, e.g., CipA (BAA32429). The preparation of cohesin polypeptide may be carried out according to the preparation of the recombinant fused proteins. For example, the domain containing the full length of CipA originating from *Clostridium josui* or the cohesin domain of CipA is cloned, and integrated into an optional expression vector to construct a cohesin polypeptide-expressing vector, the expression vector is introduced into a host to produce a cohesin polypeptide, and the resulting cohesin polypeptide is purified and isolated by means of chromatography.

Cohesin polypeptides may be purified according to a conventional method for purifying proteins. The purification method for proteins includes, for example, salting-out with ammonium sulfate, gel filtration chromatography, ion-exchange chromatography, hydrophobic interaction chromatography, hydroxyapatite chromatography, and the like. These methods may be combined with each other to give a fraction containing highly pure cohesin peptide. Specifically, hydrophobic interaction chromatography may be combined with anion-exchange chromatography to prepare a highly pure cohesin polypeptide.

The cohesin polypeptide may be immobilized by binding to a carrier according to a conventional way. For example, the cohesin polypeptide can be bound directly to a carrier through a covalent bond. Specifically, the cohesin polypeptide may be bound to an activated carrier with a crosslinking agent and the like. The activated carrier includes CNBr-activated Sepharose 4 Fast Flow, CNBr-activated Sepharose 4B, EAH Sepharose 4B, ECH Sepharose 4B, Epoxy-activated Sepharose 6B, NHS-Activated Sepharose 4FF (all are products of GE Healthcare Bioscience) and so on. Further, the cohesin polypeptide may be bound to a carrier via hydrogen bond. In such a case, CipA containing cohesin polypeptide and cellulose binding domain (CBD) is used as a cohesin polypeptide to utilize adsorption of the CBD and cellulose for binding to the cellulose carrier. The cellulose carrier includes CBinD 100 Resin (product of Novagen) and the like.

The method for binding the recombinant fused protein to a carrier on which a cohesin polypeptide is immobilized as mentioned above is not particularly limited. Examples of such methods include batch process, column method, and the like. In any process, after addition of a calcium ion to a sample containing a recombinant fused protein, the sample is exposed to a carrier on which a cohesin domain polypeptide is immobilized, and allowed to stand for a certain time if necessary to bind the recombinant fused protein alone to the carrier on which the polypeptide containing cohesin domain is immobilized, yielding a complex. Undesirable products which were not involved in formation of the complex in this operation can be removed by washing with a proper buffer solution.

Elution of the recombinant fused protein from the above complex may be achieved by addition of a proper buffer solution containing a metal chelating agent. Though the elution may be carried out at room temperature, it is particularly preferable to carry out the elution at a low temperature around 4° C. in order to prevent inactivation of the recombinant fused protein. By using the dockerin polypeptide of the invention, the elution time can be reduced to from 30 minutes to 1 hour, which has required 6 hours or more in the conventional batch process at a low temperature. In addition, in the column method, the elution peak becomes sharp, and most of the eluted protein can be recovered within 10 minutes at a flow rate of 0.5 ml/min.

The buffer solution for use in the above-mentioned elution may be the same as those used in the purification with the known dockerin and cohesin, including Good's buffer, phosphate buffer, and the like. The metal chelating agent includes EDTA, EGTA, and the like. The content of the metal chelating agent in the buffer may be about 50 mM for EDTA and about 5 mM for EGTA.

In order to facilitate the above purification method of the invention, a purification kit for the recombinant fused protein, which comprises an expression vector integrated with a polynucleotide coding for the above dockerin polypeptide and a carrier on which a polypeptide containing cohesin domain is immobilized, may be utilized.

EXAMPLES

The following examples serve to illustrate the invention in detail but are not intended to limit the scope of the invention.

Example 1

Preparation of a Gene Coding for a Dockerin Polypeptide

A gene coding for a dockerin polypeptide wherein, in the amino acid sequence (SEQ ID NO: 1) of the wild-type dockerin originating from the CelB of *Clostridium josui* as described below, the 16th amino acid leucine (L) from the first amino acid metionine (14th amino acid of the subdomain 1 of dockerin) and/or the 49th amino acid isoleucine (I) from the first amino acid metionine (14th amino acid of the subdomain 2 of dockerin) was substituted with an amino acid as shown in the following Table 1, was prepared as follows.

TABLE 1

|  | 16th Amino acid | 49th Amino acid |
|---|---|---|
| Wild Type | L | I |
| I49T | L | T |

TABLE 1-continued

| | 16th Amino acid | 49th Amino acid |
|---|---|---|
| I49G | L | G |
| I49S | L | S |
| I49N | L | N |
| L16T/I49T | T | T |
| I49Y | L | Y |
| L16G/I49G | G | G |
| I49V | L | V |

The above-mentioned amino acid substitution was carried out utilizing an overlapping extension method (Mikaelian, et al., Nucl. Acids Res., 20, 376 (1992)). The following describes PCR primers and the like used in the overlapping extension method. In this connection, the preparation of PCR samples and the PCR conditions in the following Examples were carried out in the same manner as mentioned below unless otherwise stated. The PCR primers for N-terminal fusion as shown below mean those in which a restriction enzyme NcoI recognition sequence is added to the 5'-end of dockerin for insertion to a transfer vector and further a restriction enzyme NheI recognition sequence is added to the 3'-end, and the primers for C-terminal fusion mean those in which a restriction enzyme Eco81I recognition sequence is added to the 5'-end of dockerin for insertion to a transfer vector and further a restriction enzyme SnaBI recognition sequence is added to the 3'-end.

```
<PCR Primers>
Primers for the N-terminal fusion
nDock 1 primer: (addition of restriction enzyme
NcoI sequence)
5'-gatccATgggTTTAAAAggCgATgTCAATAATg-3' nDock 2 primer: (addition of restriction enzyme
NheI sequence)
5'-cttCCGctagcATTcAGcAGTTTAAcTTTTAGcTG-3'

Primers for the C-terminal fusion
cDock 1 primer: (addition of restriction enzyme
Eco81I sequence)
5'-CTggCCTCAggATgggTTTAAAAgg-3' cDock 2 primer: (addition of restriction enzyme
SnaBI sequence)
5'-GAATTATTAAAATACGTACAACAATTGTCTGTAAATC-3'

Primer set for substitution of L16T
L16T sense primer:
5'-ggTgCTATAgATgCCacTgATATTgCTgCg-3'

L16T anti-sense primer:
5'-cGcAGcAATATcAgtGGcATcTATAGcAcc-3'

Primer set for substitution of I49T
I49T sense primer:
5'-cggAAATATTgATgCCAcTgATTTTgCTCAg-3'

I49T anti-sense primer:
5'-cTGAGcAAAATcAgTGGcATcAATATTTccg-3'

Primer set for substitution of I49G
I49G sense primer:
5'-ggAAATATTgATgCCggcgATTTTgCTCAg-3'

I49G anti-sense primer:
5'-cTGAGcAAAATcgccGgcATcAATATTTcc-3'

Primer set for substitution of I49S
I49S sense primer:
5'-ggAAATATTgATgCCtccgATTTTgCTCAg-3'

I49S anti-sense primer:
5'-cTGAGcAAAATcggaGgcATcAATATTTcc-3'

Primer set for substitution of I49N
I49N sense primer:
5'-ggAAATATTgATgCCaaTgATTTTgCTCAg-3'

I49N anti-sense primer:
5'-cTGAGcAAAATcAttGgcATcAATATTTcc-3'

Primer set for substitution of L16G
L16G sense primer:
5'-ggTgCTATAgATgCCggTgATATTgCTgCg-3'

L16G anti-sense primer:
5'-cGcAGcAATATcAccGGcATcTATAGcAcc-3'

Primer set for substitution of I49Y
I49Y sense primer:
5'-cggAAATATTgATgCCtAcgATTTTgCTCAg-3'

I49Y anti-sense primer:
5'-cTGAGcAAAATcgTAGGcATcAATATTTccg-3'

Primer set for substitution of I49V
I49V sense primer:
5'-ggAAATATTgATgcCgTTgATTTTgCTCAg-3'

I49V anti-sense primer:
5'-cTGAGcAAAATcAAcGgcATcAATATTTcc-3'
```

<Composition of PCR Sample>

| | |
|---|---|
| Vector as template | 1 ng |
| 10-Fold KOD-Plus-(Toyobo) buffer | 5 μl |
| Primer (10 μM each) | 1.5 μl |
| 2 mM dNTP mixture (Toyobo) | 5 μl |
| 2.5 mM Magnesium sulfate | 2 μl |
| KOD-Plus-(Toyobo) buffer | 1 μl |
| Distilled water (added up to 50 μl total) | |

<PCR Condition>
Step 1: 94.0° C., 2 minutes
Step 2: 94.0° C., 15 seconds
Step 3: 52.0° C., 30 seconds
Step 4: 68.0° C., 1 minute/1 kbp
Step 5: The steps 2-4 are repeated 30 times.

(1) Synthesis of the I49T-Substituted Dockerin Polypeptide Gene for the N-Terminal Fusion A gene sequence (BAA04078) of wild-type dockerin originating from the CelB of *Clostridium josui* was integrated into a transfer vector pM000001 (Katakura Industries) for preparation of recombinant baculovirus at the upper stream of a multicloning site to prepare a vector pMONDT10. Using pM0NDT10 as a template and the above-mentioned nDock 1 primer and I49T anti-sense primer, a gene coding for the first half sequence of dockerin was synthesized by means of PCR. Similarly, a gene coding for the latter half sequence of dockerin was synthesized by means of PCR using the nDock 2 primer and I49T sense primer. Using the gene coding for the first half of dockerin polypeptide and the gene coding for the latter half, the following PCR sample for gene binding was prepared, and the gene coding for the first half of dockerin and the gene coding for the latter half were annealed in a PCR condition for gene binding. The nDock 1 primer and nDock 2 primer were added to the sample after annealing, and PCR was carried out using the annealed gene as a template to synthesize a gene coding for dockerin polypeptide for the N-terminal fusion in which the 49th amino acid I of the wild-type dockerin was substituted with T (hereinafter, referred to as an "I49'-substituted gene for the N-terminal fusion").

<Composition of PCR Sample for Gene Binding>

| | |
|---|---|
| Gene coding for the first half of dockerin polypeptide | 1 µl |
| Gene coding for the latter half of dockerin polypeptide | 1 µl |
| 10-Fold KOD-Plus-(Toyobo) buffer | 5 µl |
| 2 mM dNTP mixture (Toyobo) | 5 µl |
| 2.5 mM Magnesium sulfate | 2 µl |
| KOD-Plus-(Toyobo) buffer | 1 µl |
| Distilled water | 32 µl |

<PCR Condition for Gene Binding>
Step 1: 94° C., 15 seconds
Step 2: 52° C., 30 seconds
Step 3: 74° C., 30 seconds
Step 4: The steps 1-3 are repeated 2 times.

(2) Synthesis of the I49G-Substituted Dockerin Polypeptide Gene for the N-Terminal Fusion An I49G-substituted dockerin polypeptide gene for the N-terminal fusion in which the 49th amino acid I of the wild-type dockerin was substituted with G (hereinafter, referred to as "I49G-substituted gene for the N-terminal fusion") was synthesized in the same manner as in the above section (1), except that a primer set for the I49G substitution was used in place of the primer set for the I49T substitution.

(3) Synthesis of the I49S-substituted dockerin polypeptide Gene for the N-Terminal Fusion An I49S-substituted dockerin polypeptide gene for the N-terminal fusion in which the 49th amino acid I of the wild-type dockerin was substituted with S (hereinafter, referred to as "I49S-substituted gene for the N-terminal fusion") was synthesized in the same manner as in the above section (1), except that a primer set for the I49S substitution was used in place of the primer set for the I49T substitution.

(4) Synthesis of the I49N-Substituted Dockerin Polypeptide Gene for the N-Terminal Fusion An I49N-substituted dockerin polypeptide gene for the N-terminal fusion in which the 49th amino acid I of the wild-type dockerin was substituted with N (hereinafter, referred to as "I49N-substituted gene for the N-terminal fusion") was synthesized in the same manner as in the above section (1), except that a primer set for the I49N substitution was used in place of the primer set for the I49T substitution.

(5) Synthesis of the I49Y-Substituted Dockerin Polypeptide Gene for the N-Terminal Fusion An I49Y-substituted dockerin polypeptide gene for the N-terminal fusion in which the 49th amino acid I of the wild-type dockerin was substituted with Y (hereinafter, referred to as "I49Y-substituted gene for the N-terminal fusion") was synthesized in the same manner as in the above section (1), except that a primer set for the I49Y substitution was used in place of the primer set for the I49T substitution.

(6) Synthesis of the I49V-Substituted Dockerin Polypeptide Gene for the N-Terminal Fusion An I49V-substituted dockerin polypeptide gene for the N-terminal fusion in which the 49th amino acid I of the wild-type dockerin was substituted with V (hereinafter, referred to as "I49V-substituted gene for the N-terminal fusion") was synthesized in the same manner as in the above section (1), except that a primer set for the I49V substitution was used in place of the primer set for the I49T substitution.

(7) Synthesis of the L16G/I49G-Substituted Dockerin Polypeptide Gene for the N-Terminal Fusion A gene coding for the first half sequence of dockerin was synthesized by means of PCR using the above-described nDock 1 primer and L16G anti-sense primer and the I49G-substituted gene for the N-terminal fusion prepared in the above section (2) as a template. Similarly, a gene coding for the latter half sequence of dockerin was synthesized by means of PCR using the nDock 2 primer and L16G sense primer. The above-mentioned PCR sample for gene binding was prepared using the gene coding for the first half of dockerin and the gene coding for the latter half, and the gene coding for the first half of dockerin and the gene coding for the latter half were annealed in the above-mentioned PCR condition for gene binding. The nDock 1 primer and nDock 2 primer were added to the sample after annealing, and PCR was carried out using the annealed gene as a template to synthesize a gene coding for dockerin polypeptide for the N-terminal fusion in which the 16th amino acid L of the wild-type dockerin was substituted with G, and the 49th amino acid I with G (hereinafter, referred to as a "L16G/I49G-substituted gene for the N-terminal fusion").

(8) Synthesis of the L16T/I49T-Substituted Dockerin Polypeptide Gene for the N-Terminal Fusion A gene coding for the first half sequence of dockerin was synthesized by means of PCR using the above-described nDock 1 primer and L16T anti-sense primer and the I49T-substituted gene for the N-terminal fusion prepared in the above section (1) as a template. Similarly, a gene coding for the latter half sequence of dockerin was synthesized by means of PCR using the nDock 2 primer and L16T sense primer. The above-mentioned PCR sample for gene binding was prepared using the gene coding for the first half of dockerin and the gene coding for the latter half, and the gene coding for the first half of dockerin and the gene coding for the latter half were annealed in the above-mentioned PCR condition for gene binding. The nDock 1 primer and nDock 2 primer were added to the sample after annealing, and PCR was carried out using the annealed gene as a template to synthesize a gene coding for dockerin polypeptide for the N-terminal fusion in which the 16th amino acid L of the wild-type dockerin was substituted with T, and the 49th amino acid I with T (hereinafter, referred to as an "L16T/I49T-substituted gene for the N-terminal fusion").

(9) Synthesis of the I49T-Substituted Dockerin Polypeptide Gene for the C-Terminal Fusion A gene sequence (BAA04078) of wild-type dockerin originating from the CelB of *Clostridium josui* was integrated into a transfer vector pM000001 (Katakura Industries) for preparation of recombinant baculovirus at the down stream of a multicloning site in a conventional way to prepare a vector pMOCDT17. Using pMOCDT17 as a template and the above-mentioned cDock 1 primer and I49T anti-sense primer, a gene coding for the first half sequence of dockerin was synthesized by means of PCR. Similarly, a gene coding for the latter half sequence of dockerin was synthesized by means of PCR using the cDock 2 primer and I49T sense primer. The above-mentioned PCR sample for gene binding was prepared using the gene coding for the first half of dockerin and the gene coding for the latter half, and the gene coding for the first half of dockerin and the gene coding for the latter half were annealed in the above-mentioned PCR condition for gene binding. The cDock 1 primer and cDock 2 primer were added to the sample after annealing, and PCR was carried out using the annealed gene as a template to synthesize a gene coding for dockerin polypeptide for the C-terminal fusion in which the 49th amino acid I of the wild-type dockerin was substituted with T (hereinafter, referred to as an "I49T-substituted gene for the C-terminal fusion").

(10) Synthesis of the L16T/I49T-Substituted Dockerin Polypeptide Gene for the C-Terminal Fusion A gene coding for the first half sequence of dockerin was synthesized by means of PCR using the above-described cDock 1 primer and L16T anti-sense primer and the I49T-substituted gene for the C-terminal fusion synthesized in the above section [[(8)]] (9) as a template. Similarly, a gene coding for the latter half sequence of dockerin was synthesized by means of PCR using the cDock 2 primer and L16T sense primer. The above-mentioned PCR sample for gene binding was prepared using the gene coding for the first half of dockerin and the gene coding for the latter half, and the gene coding for the first half of dockerin and the gene coding for the latter half were annealed in the above-mentioned PCR condition for gene binding. The cDock 1 primer and cDock 2 primer were added to the sample after annealing, and PCR was carried out using the annealed gene as a template to synthesize a gene coding for dockerin polypeptide for the C-terminal fusion in which the 16th amino acid L of the wild-type dockerin was substituted with T, and the 49th amino acid I with T (hereinafter, referred to as an "L 16T/I49T-substituted gene for the C-terminal fusion").

Example 2

Construction of Transfer Vectors (1)

(1) Purification of the I49T-Substituted Gene for the N-Terminal Fusion 8-24U of restriction enzymes NcoI and NheI (both are the products of Takara Bio) were added to 5 μl of the PCR product of the I49T-substituted gene for the N-terminal fusion synthesized in Example 1(1) for restrictive digestion to expose the terminal sequences. Then, this was passed through a Qiagen spin column (QIAquick; Qiagen) to purify the I49T-substituted gene for the N-terminal fusion treated with restriction enzymes.

(2) Insertion of the I49T-Substituted Gene for the N-Terminal Fusion into a Transfer Vector The restriction enzyme-recognition sites NcoI/NheI of pM0NDT10 prepared in Example 1(1) were cleaved with restriction enzymes NcoI and NheI (both are the products of Takara Bio) to yield a linear transfer vector, and then the ends cleaved with the restriction enzymes were dephosphorylated with alkaline phosphatase (Takara Bio). This transfer vector (0.1 μg; 2 μl) was combined with the I49T-substituted gene for the N-terminal fusion (0.1 μg; 3 μl) which was purified in the above section (1), and allowed to react using a ligation kit (Takara Bio) at 16° C. for 1 hour, and the whole reaction mixture was used in the transformation of *Escherichia coli* DH5α (Invitrogen). From this transformant, an ampiciillin-resitant transformant was selected in a conventional manner and then applied to purification of the plasmid. Then, the base sequences of some clones were confirmed by reacting with the following Yng. forward primer using an ABI sequence kit (product of ABI) and analyzing whether the I49T-substituted gene for the N-terminal fusion was introduced using a DNA sequencer (product of ABI). The clone in which the I49T-substituted gene for the N-terminal fusion was introduced and no mutation occurred in other portion was used as pM0NDT10-DV(I49T) vector.

Using the genes synthesized in Example 1(2)-(8), the following vectors were defined in the same manner as mentioned above (FIG. 1): pM0NDT10-DV (I49G), vector in which the I49G-substituted gene for the N-terminal fusion is inserted; pM0NDT10-DV (I49S), vector in which the I49S-substituted gene for the N-terminal fusion is inserted; pM0NDT10-DV (I49N), vector in which the I49N-substituted gene for the N-terminal fusion is inserted; pM0NDT10-DV (I49Y), vector in which the I49Y-substituted gene for the N-terminal fusion is inserted; pM0NDT10-DV (I49V), vector in which the I49V-substituted gene for the N-terminal fusion is inserted; pM0NDT10-DV (L16G/I49G), vector in which the L16G/I49G-substituted gene for the N-terminal fusion is inserted; and pM0NDT10-DV (L16T/I49T), vector in which the L16T/I49T-substituted gene for the N-terminal fusion is inserted.

Primer for Confirmation of the Base Sequence of Clone

```
Yng. forward primer:
5'-aaccatctcgcaaataaata-3'
```

Example 3

Construction of Transfer Vectors (2)

(1) Preparation of the I49T-Substituted Gene for the C-Terminal Fusion 8-24U of restriction enzymes Eco81I and SnaBI (both are the products of Takara Bio) were added to 5 ml of the PCR product of the I49T-substituted gene for the C-terminal fusion synthesized in Example 1 (91 for restrictive digestion to expose the terminal sequences. Then, this was passed through a Qiagen spin column (QIAquick; Qiagen) to purify the I49T-substituted gene for the C-terminal fusion treated with restriction enzymes.

(2) Insertion of the I49T-Substituted Gene for the C-Terminal Fusion into a Transfer Vector The restriction enzyme-recognition sites Eco81I/SnaBI of pM0CDT17 prepared in Example 1 (9) were cleaved with restriction enzymes Eco81I and SnaBI (both are the products of Takara Bio) to yield a linear transfer vector, and then the ends cleaved with the restriction enzymes were dephosphorylated with alkaline phosphatase (Takara Bio). This transfer vector (0.1 mg; 2 ml) was combined with the I49T-substituted gene for the C-terminal fusion (0.1 mg; 3 ml) which was purified in the above section (1), and allowed to react using a ligation kit (Takara Bio) at 16° C. for 1 hour, and the whole reaction mixture was used in the transformation of *Escherichia coli* DH5a (Invitrogen). From this transformant, an ampicillin-resitant transformant was selected in a conventional manner and then applied to purification of the plasmid. Then, the base sequences of some clones were confirmed by reacting with the above-mentioned Yng. forward primer using an ABI sequence kit (product of ABI) and analyzing whether the I49T-substituted gene for the C-terminal fusion was introduced using a DNA sequencer (product of ABI). The clone in which the I49T-substituted gene for the C-terminal fusion was introduced and no mutation occurred in other portion was used as pM0CDT17-DV(I49T) vector.

Using the gene synthesized in Example 1 (10), the vector in which the L16T/I49T-substituted gene for the C-terminal fusion was inserted, was defined as pM0CDT17-DV (L16T/I49T) in the same manner as mentioned above (FIG. 2).

Example 4

Preparation of Recombinant Fused Proteins (1) Acquisition of the JNK3 Gene

Using as a template a vector FLJ42801 (Japan Biological Informatics Consortium (JBiC)) in which a protein kinase JNK3 (mitogen-activated protein kinase 10 isoform 3) was inserted, PCR was carried out with the JNK3-5' primer and the JNK3-3' TGA primer for use in preparation of JNK3 gene. Restriction enzymes XhoI and EcoRV (both are the products of Takara Bio) were added to 5 μl of the PCR product in which a restriction enzyme XhoI recognition sequence was added to the 5' end of the JNK3 gene and a restriction enzyme EcoRV recognition sequence to the 3' end, for restrictive digestion to expose the terminal sequences. Then, this restriction enzyme-treated JNK3 gene was purified with a Qiagen spin column (QIAquick; Qiagen).

Primers for Preparation of the JNK3 Gene

```
JNK3-5' primer (with the restriction enzyme XhoI
sequence):
5'-gatctcgagatgagcaaaagcaaagttg-3'

JNK3-3' TGA primer (with the restriction enzyme
EcoRV sequence):
5'-gcgatatctcactgctgcacctgtgctgaag-3'
```

(2) Insertion of the JNK3 Gene into a Transfer Vector

A variety of transfer vectors prepared in Examples 2 and 3 were respectively digested with XhoI and EcoRV (both are the products of Takara Bio), into which was inserted the JNK3 gene using a ligation kit (Takara Bio) to yield transfer vectors for expression of recombinant fused proteins. *Escherichia coli* DH5α (Invitrogen) was transformed with these transfer vectors, and the ampicillin-resistant clones were purified with plasmid. Further, insertion of the JNK3 gene, the correctness of reading frame, and no mutation in the JNK3 gene were confirmed by a DNA sequencer (product of ABI).

(3) Preparation of a Virus for Expressing a Recombinant Fused Protein

The transfer vector for expressing a recombinant fused protein prepared in the above section (2) and the DNA of ABvNPV (Katakura Industries) linearized with Eco81I (Takara Bio) were mixed in the ratio of 2.5:1 (mass ratio) in a TC-100 culture medium (serum-free) and co-transfected to Bm-N cells (cultured in a TC-100 medium) together with a cationic lipid reagent (Lipofectin® reagent; Invitrogen). Incubation was carried out in standing at 25° C. for 7 days, and the culture supernatant was used as a stock solution of virus for expressing the recombinant fused protein.

(4) Expression of the Recombinant Fused Protein

The stock solution of virus for expressing the recombinant fused protein prepared in the above section (3) was inoculated into 2 pupae of silkworm (Kinshu Showa) using a Terumo syringe, and the pupae on 7th day were recovered, frozen for preservation, and used as virus-infected silkworm for expressing the recombinant fused protein. The two silkworms were placed in a 50 ml tube, into which were added 10 ml of PBS containing 10 mass % (hereinafter merely "%") glycerol, one stainless bead, 5 g of zirconia bead, 100 μl of 500 mM 2-mercaptoethanol, 100 μl of 1 M benzamine and 100 μl of 100 mM PMSF. The mixture was homogenized by a homogenizer at 4° C. for 3 minutes. This homogenized suspension was centrifuged at 3,000 rpm for 10 minutes at 4° C. and filtered through a sheet of gauze to give a supernatant. This supernatant was applied to an ultra-centrifuge (BECK-MAN COULTER Avantie Centrifuge HP-30I) at 100,000 g for 60 minutes to give an ultra-centrifuged supernatant containing the recombinant fused protein.

Example 5

Preparation of the Recombinant Cohesin and the Construction of a Cohsin Column (1) Preparation of the Recombinant Cohesin Baculovirus in which the CipA gene (BAA32429) of *Clostridium josui* was integrated was prepared in the same manner as in the above-mentioned Example 4, and this virus solution was inoculated into 2 pupae of silkworm (Kinshu Showa) using a Terumo syringe. After inoculation of virus, the silkworms at the 7th day were recovered, frozen for preservation, and used as virus-infected silkworm for expressing the recombinant cohesin. The two silkworms were placed in a 50 ml tube, into which were added 10 ml of PBS containing 10% glycerol, 1 stainless bead, 5 g of zirconia bead, 100 μl of 500 mM 2-mercaptoethanol, 100 μl of 1 M benzamine and 100 μl of 100 mM PMSF. The mixture was homogenized by a homogenizer at 4° C. for 3 minutes. This homogenized suspension was centrifuged at 3,000 rpm for 10 minutes at 4° C. and filtered through a sheet of gauze to give a supernatant. This supernatant was applied to an ultra-centrifuge (BECK-MAN COULTER Avanti® Centrifuge HP-301) at 100,000 g for 60 minutes to give an ultra-centrifuged supernatant containing the recombinant cohesin.

(2) Purification of the Recombinant Cohesin

The ultra-centrifuged supernatant prepared as above was diluted with 4-fold volume of Buffer A (containing 50 mM potassium hydrogen phosphate-hydrochloric acid and 1 M ammonium sulfate, pH 6.8), and filtered through a 0.45 μm filter. The resulting filtrate was applied to a column of hydrophobic interaction chromatography (Phenyl Sepharose HP: GE Healthcare Bioscience) equilibrated with Buffer A. By this operation, the recombinant cohesin was adsorbed on the carrier. The proteins unadsorbed on the carrier (non-adsorbed proteins) were washed out with Buffer A, and then the recombinant cohesin was eluted with ammonium sulfate by linearly changing the concentration from 1 M to 0 M. The fractions eluted with about 0.3-0.2 M ammonium sulfate were recovered.

The fractions containing the recombinant cohesin obtained by hydrophobic interaction chromatography were collected respectively, then dialyzed against Buffer B (containing 50 mM potassium hydrogen phosphate-hydrochloric acid, pH 6.0), and filtered through a 0.45 μm filter. The resulting filtrate was applied to and adsorbed on a column for anion exchange chromatography (Q-Sepharose HP: GE Healthcare Bioscience) equilibrated with Buffer B. After the unadsorbed proteins were washed out with Buffer A, the adsorbed recombinant cohesin was eluted with potassium chloride by linearly changing the concentration from 0 to 1M, and the fraction eluted with about 0.1 M potassium chloride was recovered.

The fractions containing the recombinant cohesin obtained by the above-mentioned anion-exchange chromatography were respectively collected and applied to a centrifugal filtration membrane (Centricon plus-20 Biomax-5 membrane; Millipore) to concentrate the protein solution and exchange with a potassium phosphate buffer (pH 8.0), yielding a purified product of the recombinant cohesin.

(3) Preparation of Cohesin-Fused NHS-Sepharose

The purified product of the recombinant cohesin prepared as above was adsorbed on NHS-Sepharose (NHS-Activated Sepharose 4FF: GE Healthcare Bioscience) via covalent binding for small-scale batch purification. The NHS-Sepharose fused with the recombinant cohesin (hereinafter referred to as "cohesin carrier") was preserved in a buffer solution (containing 25 mM Tris-hydrochloric acid, 250 mM sodium chloride and 2.5 mM calcium chloride, pH 7.4) at 4° C. The roughly purified product of the recombinant cohesin was adsorbed on a column (HiTrap NHS-activated HP: GE Healthcare Bioscience) for purification with a chromatographic system (AKTAprime: GE Healthcare Bioscience).

Example 6

Comparative Test for Purification of the Recombinant Fused Cohesin

200 µl of cohesin carrier prepared in Example 5 and 600 µl of buffer for binding (containing 25 mM Tris-hydrochloric acid, 250 mM sodium chloride and 2.5 mM calcium chloride) were added to 200 µl each of the ultra-centrifuged supernatant containing the recombinant fused protein prepared in Example 4, and the mixture was agitated on a rotary shaker for 1 hour. Thereafter, the mixture was centrifuged at 3,000 rpm for 5 minutes to remove the supernatant. Then, 1 ml of washing buffer (containing 25 mM Tris-hydrochloric acid and 250 mM sodium chloride) was added carrier to wash the cohesin carrier. After washing, 200 µl of elution buffer (containing 25 mM Tris-hydrochloric acid, 250 mM sodium chloride and 5 mM EGTA) was added to the cohesin carrier to elute the recombinant fused protein. The eluate 15 µl each was collected as sample after a lapse of 5 minutes, 30 minutes, 1 hour and 6 hours. The above operation was conducted at 4° C. in every case.

The above samples were separated by means of SDS-PAGE using electrophoretic gel (Perfect NT Gel A 10-20%; product of DRC). FIG. 3 shows the results of SDS-PAGE conducted for a sample containing the recombinant JNK3 of which an L16T/I49T-substituted dockerin polypeptide was fused at the N-terminal and for a sample containing the recombinant JNK3 of which a wild-type dockerin was fused at the N-terminal. FIG. 4 shows the results of SDS-PAGE conducted for a sample containing the recombinant JNK3 of which an L16T/I49T-substituted dockerin polypeptide was fused at the C-terminal and for a sample containing the recombinant JNK3 of which a wild-type dockerin was fused at the C-terminal.

In the recombinant JNK3 of which a wild-type dockerin was fused at the N-terminal, as seen from the lanes 6-9 in FIG. 3(A), the amount of elution was increased with a lapse of time and reached the peak after 6 hours in the lane 9. On the other hand, in the recombinant JNK3 of which an L16T/I49T-substituted dockerin polypeptide was fused at the N-terminal, it was shown that the amount of elution reached the peak after 30 minutes in the lane 7. Further, there was no influence of the substitution of the amino acid in a wild-type dockerin on the purity after purification.

In the recombinant JNK3 of which a wild-type dockerin was fused at the C-terminal, as seen from the lanes 6-9 in FIG. 4(A), the amount of elution was increased with a lapse of time and reached the peak after 6 hours in the lane 9. On the other hand, in the recombinant JNK3 of which an L16T/I49T-substituted dockerin polypeptide was fused at the C-terminal, it was shown that the amount of elution reached the peak after 30 minutes in the lane 7. Further, there was no influence of the substitution of the amino acid in a wild-type dockerin on the purity after purification.

In addition, in the cases where the other dockerin polypeptides (I49T, I49G, I49N, I49S, and I49V) originating from wild-type dockerins in which an amino acid was substituted were fused at the N-terminal of JNK3, the same comparative test for purification was carried out to obtain the rate of elution on each time by means of a densitometric analysis (CS Analyzer; product of ATTO), wherein the amount of elution after 6 hours (maximum amount of elution) was regarded as 100 (Table 2). The results showed that, in every case except I49V, the dockerin polypeptide-fused proteins were eluted almost completely after 30 minutes from the start of elution. Further, even in the cases where a dockerin polypeptide was fused at the C-terminal of JNK3, the same results were shown (Table 3).

TABLE 2

| | Rate of eluted recombinant protein with a lapse of elution time (%) | | | |
|---|---|---|---|---|
| | 5 min | 30 min | 60 min | 360 min |
| Wild type | 11.5 | 28.8 | 39.6 | 100 |
| I49T | 66.5 | 100 | 100 | 100 |
| I49G | 100 | 100 | 100 | 100 |
| I49N | 65.9 | 94.1 | 100 | 100 |
| I49S | 74.7 | 100 | 100 | 100 |
| L16T/I49T | 55.2 | 100 | 100 | 100 |
| I49V | 25.3 | 53.3 | 68.2 | 100 |

TABLE 3

| | Rate of eluted recombinant protein with a lapse of elution time (%) | | | |
|---|---|---|---|---|
| | 5 min | 30 min | 60 min | 360 min |
| Wild type | 1.5 | 10.5 | 20.9 | 100 |
| I49T | 83.1 | 100 | 100 | 100 |
| L16T/I49T | 55.7 | 100 | 100 | 100 |

In order to confirm the effect of mutation of dockerin on purification with a column, the following experiment was performed. The column (HiTrap NHS-activated HP) prepared in Example 5 was installed in a chromatographic system (AKTAprime). The ultra-centrifuged supernatant (0.1 ml each) containing the recombinant JNK3 of which the I49G-substituted dockerin polypeptide was fused at the N-terminal prepared in Example 4, was diluted 5 times with a buffer for binding (containing 25 mM Tris-hydrochloric acid, 250 mM sodium chloride, 1 mM calcium chloride and 10% glycerol) and allowed to flow at a rate of 1 ml per minute. Then, washing buffer (containing 25 mM Tris-hydrochloric acid, 250 mM sodium chloride and 10% glycerol) was applied to the column to remove unadsorbed fractions, and then eluting buffer (containing 25 mM Tris-hydrochloric acid, 250 mM sodium chloride, 5 mM EGTA and 10% glycerol) was applied to the column at a rate of 0.1 ml per minute to yield the recombinant fused protein. FIG. 5 showed the results. The eluate was sampled every 1 ml.

The recombinant JNK3 of which a wild-type dockerin was fused at the N-terminal was eluted continuously in the 2nd fraction to over 20th fraction from the start of elution (FIG. 5(A)). On the other hand, the elution of the recombinant JNK3 of which an I49O-substituted dockerin polypeptide was fused at the N-terminal, began in the 2nd fraction from the start and was completed in the 3rd fraction (10 minutes from the start of elution) (FIG. 5(B)). When the eluting buffer was allowed to flow at a rate of 0.5 ml per minute in the same manner as mentioned above, the recombinant JNK3 of which an I49O-substituted dockerin polypeptide was fused at the N-terminal was eluted completely within 10 minutes from the start of elution.

Example 7

Analysis of the Affinity Between the Recombinant Fused Protein and the Recombinant Cohesin by an Interaction Analysis The binding rate constant (ka) and the dissociation rate constant (kd) of the recombinant cohesin to the recombinant JNK3 of which a wild-type dockerin was fused at the N-terminal were determined by means of a surface plasmon resonance method (hereinafter abbreviated to "SPR method") using Biacore T-100 (product of Biacore). In this determination, a running buffer having the same composition as HBS-P (0.01 M HEPES (pH 7.4), 0.15 M sodium chloride and 0.005% surfactant (P20)) recommended by Biacore T-100, was used.

rProtein A (29435-14; Nacalai Tesque) was attached to a Sensor chip CM5 (Biacore) via covalent bond by means of an amine-coupling method. In this operation, the amount of immobilized rProtein A was approximately 12,000 RU. An anti-JNK3 antibody (55A8; Cell Signaling) was immobilized on this sensor chip CM5 covalently binding to rProtein A (hereinafter abbreviated to "Protein A chip") so as to be about 1,300 RU, and further captured the recombinant JNK3 of which a wild-type dockerin was fused at the N-terminal so as to be about 100 RU. The recombinant cohesin (5 nM, 10 nM or 20 nM) and calcium chloride (final concentration 1 mM) were added to analyze the interaction between the recombinant cohesin and JNK3 fused with a wild-type dockerin at the N-terminal, and the binding rate constant (ka), the dissociation rate constant (kd) and the dissociation constant ($K_D$) were determined. Table 4 shows the results. In the same manner, the interaction with the recombinant cohesin was analyzed for the recombinant proteins fused with dockerin polypeptides into which a variety of mutations (I49T, I49G, I49N, I49S, I49V, L16T/I49T) were introduced at the N-terminal of JNK3. Table 4 shows these results together.

TABLE 4

| | +Ca$^{2+}$ (without 5 mM EGTA) | | | +5 mM EGTA | | |
|---|---|---|---|---|---|---|
| | ka (1/Ms) | kd (1/s) | $K_D$ (M) | ka (1/Ms) | kd (1/s) | $K_D$ (M) |
| Wild type | 8.1E+05 | 5.3E−03 | 6.5E−09 | 2.0E+06 | 7.9E−03 | 3.9E−09 |
| I49T | 1.6E+06 | 6.0E−03 | 3.8E−09 | 1.2E+06 | 2.3E−02 | 1.9E−08 |
| I49G | 3.0E+06 | 6.6E−03 | 2.2E−09 | 3.0E+05 | 5.0E−02 | 1.7E−07 |
| I49N | 1.3E+06 | 5.0E−03 | 3.7E−09 | 1.6E+06 | 8.9E−02 | 5.6E−08 |
| I49S | 1.0E+06 | 4.5E−03 | 4.5E−09 | 7.1E+05 | 4.8E−02 | 6.7E−08 |
| L16T/I49T | 4.9E+06 | 1.5E−02 | 3.2E−09 | 2.5E+05 | 2.9E−02 | 1.2E−08 |
| I49V | 4.3E+05 | 3.3E−03 | 7.6E−09 | 1.4E+06 | 1.1E−02 | 8.1E−09 |

Further, in order to elucidate the change in the dissociation rate between cohesin and diversely-mutated dockerins caused by addition of a chelating agent, 5 mM EGTA was added to a running buffer, and the interaction between a recombinant cohesin and the dockerin into which a variety of mutations were introduced at the N-terminal of JNK3 was analyzed in the same manner. These results are shown in FIGS. 6-8 and Table 4.

The dissociation constant ($K_D$) calculated from the above results of measurement was 6.5E−09 ($K_D$) for the wild-type dockerin in the presence of calcium ion, and 3.9E−09 ($K_D$) when a chelating agent was added; thus, almost no increase in the dissociation rate by the chelating agent was observed. On the contrary, the dissociation constant in the mutant type dockerin was 3.8E−09 ($K_B$) for I49T in the presence of calcium ion, and 1.9E-08 ($K_D$) when a chelating agent was added; for I49G, 2.2E-09 ($K_D$) in the presence of calcium ion, and 1.7E-07 ($K_D$) when a chelating agent was added; for I49N, 3.7E-09 ($K_D$) in the presence of calcium ion, and 5.6E-08 ($K_D$) when chelating agent was added; for I49S, 4.5E-09 ($K_D$) in the presence of calcium ion, and 6.7E-08 ($K_D$) when a chelating agent was added; for L16T/I49T, 3.2E-09 ($K_D$) in the presence of calcium ion, and 1.2E-08 ($K_D$) when a chelating agent was added; the action of a chelating agent increased the dissociation rate as high as 10 times (maximum 100 times) in every case. On the other hand, in the dissociation constant in the presence of calcium ion, there was not much difference between the wild-type dockerin and the diversely-mutated dockerins. Thus, it was shown that the binding characteristic of dockerin with cohesin in the presence of calcium ion was not particularly changed by introduction of these mutations but changed only by the action of a chelating agent.

On the other hand, the dissociation constant in the I49V mutant dockerin was 7.6E-09 ($K_D$) in the presence of calcium ion and 8.1E-09 ($K_D$) when a chelating agent was added, indicating that it is not increased considerably by the action of a chelating agent (FIG. 8).

The above-mentioned results of interaction analysis suggest that the time for elution of the diversely mutated dockerin-fused proteins from a cohesin carrier is markedly reduced even at a low temperature when using a buffer containing a chelating agent, because the characteristics of interaction between a dockerin polypeptide and cohesin in the presence of a chelating agent are changed (increase in the dissociation rate) as the result of the substitution with a certain amino acid. Specifically, for the mutated dockerin in which a certain amino acid is substituted, there is no change in the characteristics of binding with cohesin in the presence of calcium ion, and thus, it does not decrease the adsorption efficiency of column carrier in the purification process and does not increase omission during washing. On the other hand, it was found that the affinity of binding with cohesin decreases only at the time of elution by addition of a chelating agent, and the efficiency of elution of the purified protein from the column carrier is dramatically improved even at a low temperature.

In the above Examples, the recombinant fused proteins prepared by fusing a dockerin polypeptide with a protein kinase (JNK3) as the aimed protein were analyzed. The fused proteins prepared with other protein kinases or cytokines as the aimed proteins were analyzed in the same manner, and the same results were obtained.

In addition, a recombinant fused protein in which a dockerin polypeptide prepared by substituting the 48th amino acid alanine (A) (13th of the subdomain 2 of dockerin) from the first amino acid methionine in the wild-type dockerin amino acid sequence originating from CelB of *Clostridium josui*

(SEQ ID NO: 1) with serine (S) was fused at the N-terminal of protein kinase (JNK3), was prepared in the same manner as in Examples 1-4. And the interaction between this recombinant fused protein and the recombinant cohesin prepared in the same manner as in Example 5 was analyzed in the same manner as in Example 7. As a result, the dissociation constant ($K_D$) to cohesin under the action of a chelating agent was 5.2E-09, equivalent to that of the wild-type one.

INDUSTRIAL APPLICABILITY

The dockerin polypeptide of the present invention has the same binding affinity to cohesion domain as the wild-type dockerin. When this is applied to a purification method for the recombinant fused proteins using a known wild-type dockerin and cohesin, the elution time is markedly reduced at a low temperature, at which the activity of recombinant fused protein is scarcely affected. Thus, the present invention is highly practical since the effect gives a sharp elution peak in purification using a column and yields a highly concentrated pure protein within a short period of time.

Therefore, the method of purifying recombinant fused proteins using a dockerin polypeptide of the present invention allows efficient and economical purification of recombinant fused proteins.

BRIEF DESCRIPTION OF DRAWINGS

FIG. 1 shows a block diagram of a vector for the N-terminal fusion in dockerin polypeptide (underline: amino acid involved in calcium binding; frame: substituted amino acid). The vector encodes the dockerin polypeptide as follows:

| Vector | Polypeptide |
|---|---|
| pM0NDT10 | SEQ ID NO: 1 |
| pM0NDT10-DV(I49T) | SEQ ID NO: 4 |
| pM0NDT10-DV(I49G) | SEQ ID NO: 5 |
| pM0NDT10-DV(I49S) | SEQ ID NO: 6 |
| pM0NDT10-DV(I49N) | SEQ ID NO: 7 |
| pM0NDT10-DV(L16T, I49T) | SEQ ID NO: 8 |
| pM0NDT10-DV(I49Y) | SEQ ID NO: 9 |
| pM0NDT10-DV(L16G, I49G) | SEQ ID NO: 10 |
| pM0NDT10-DV(I49V) | SEQ ID NO: 11 |

Figure 2:
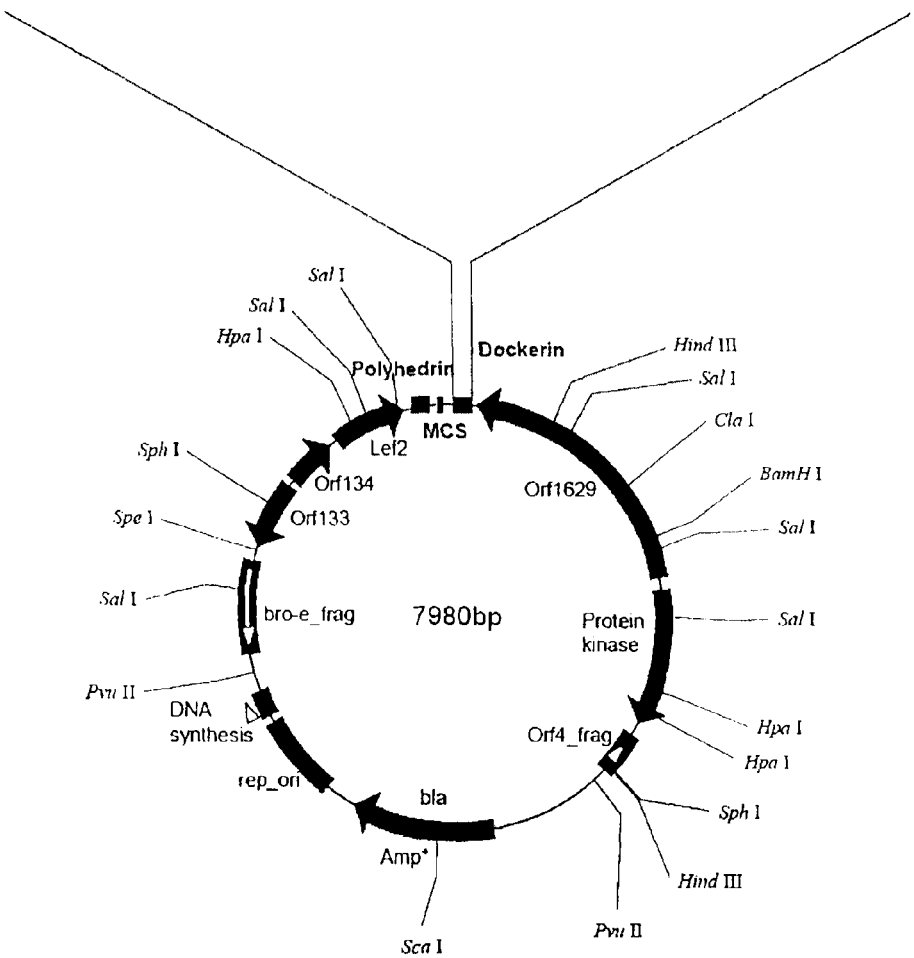

FIG. 2 shows a block diagram of a vector for the C-terminal fusion in dockerin polypeptide (underline: amino acid involved in calcium binding; frame: substituted amino acid). The vector encodes the dockerin polypeptide as follows:

| Vector | Polypeptide |
|---|---|
| pM0CDT17 | SEQ ID NO: 1 |
| pM0CDT17-DV(I49T) | SEQ ID NO: 4 |
| pM0CDT17-DV(L16T, I49T) | SEQ ID NO: 8 |

Figure 3:
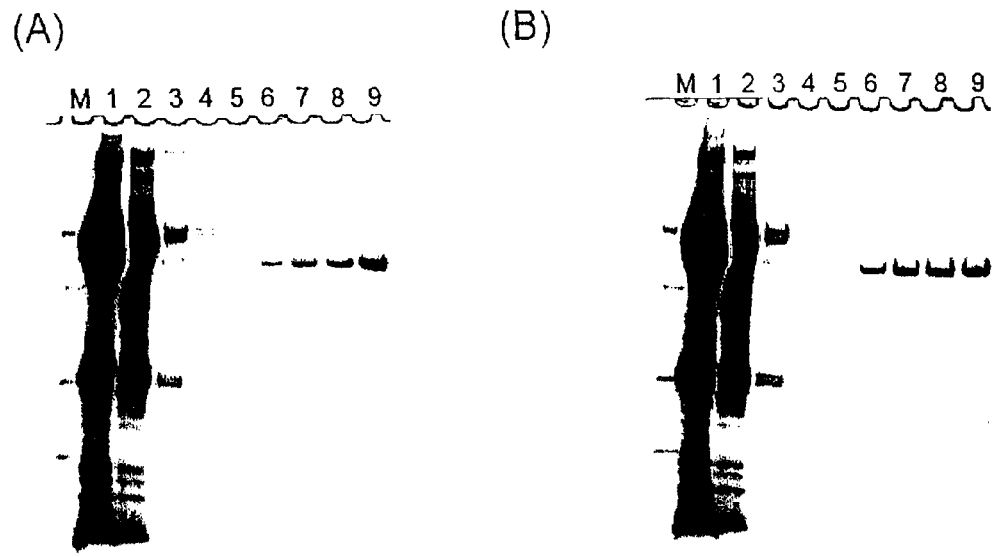

FIG. 3 shows the results of SDS-PAGE ((A) the result for a sample containing a recombinant JNK3 of which a wild-type dockerin is fused at the N-terminal; (B) the result for a sample containing a recombinant JNK3 in which an L16T/I49T-substituted dockerin polypeptide is fused at the N-terminal; Lane M: molecular weight marker (magic marker); Lane 1: the ultra-centrifuged supernatant of a pupae homogenized solution in which a recombinant fused protein was expressed; Lane 2: a fraction after the recombinant fused protein of Lane 1 was bound to a cohesin carrier; Lane 3: the washed fraction 1 of cohesin carrier; Lane 4: the washed fraction 2 of cohesin carrier; Lane 5: the washed fraction 3 of cohesin carrier; Lane 6: a fraction of the recombinant fused protein eluted with a buffer containing EGTA (5 minutes); Lane 7: a fraction of the recombinant fused protein eluted with a buffer containing EGTA (30 minutes); Lane 8: a fraction of the recombinant fused protein eluted with a buffer containing EGTA (1 hour); Lane 9: a fraction of the recombinant fused protein eluted with a buffer containing EGTA (6 hours)).

Figure 4:
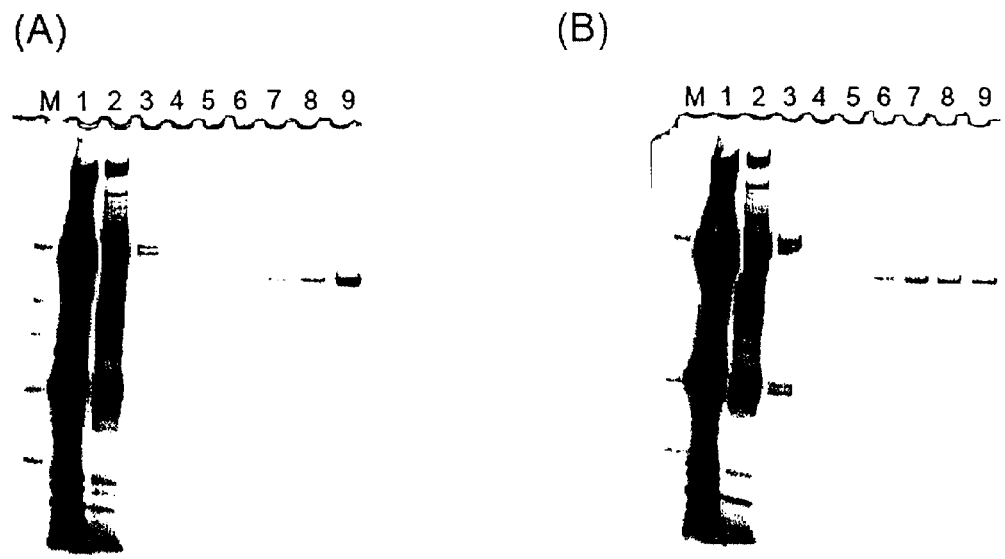

FIG. 4 shows the results of SDS-PAGE ((A) the result for a sample containing a recombinant JNK3 of which a wild-type dockerin is fused at the C-terminal; (B) the result for a sample containing a recombinant JNK3 in which an L16T/I49T-substituted dockerin polypeptide is fused at the C-terminal; Lane M: molecular weight marker (magic marker); Lane 1: the ultra-centrifuged supernatant of a pupae homogenized solution in which a recombinant fused protein was expressed; Lane 2: a fraction after the recombinant fused protein of Lane 1 was bound to a cohesin carrier; Lane 3: the washed fraction 1 of cohesin carrier; Lane 4: the washed fraction 2 of cohesin carrier; Lane 5: the washed fraction 3 of cohesin carrier; Lane 6: a fraction of the recombinant fused protein eluted with a buffer containing EGTA (5 minutes); Lane 7: a fraction of the recombinant fused protein eluted with a buffer containing EGTA (30 minutes); Lane 8: a fraction of the recombinant fused protein eluted with a buffer containing EGTA (1 hour); Lane 9: a fraction of the recombinant fused protein eluted with buffer containing EGTA (6 hours)).

FIG. 5 shows the results of purification of a recombinant fused protein using a chromatographic system ((A) the result for a sample containing a recombinant JNK3 of which a wild-type dockerin is fused at the N-terminal; (B) the result for a sample containing a recombinant JNK3 of which an I49G-substituted dockerin polypeptide is fused at the N-terminal).

FIG. 6 shows the results of analysis of the interaction between a cohesin and diversely mutated dockerins by a surface plasmon resonance method. The result for the addition of calcium ion is shown in parallel to that for a chelating agent ((A) the results of analysis of the interaction between the recombinant cohesin and the recombinant JNK3 of which a wild-type dockerin was fused at the N-terminal; (B) the results of analysis of the interaction between the recombinant cohesin and the recombinant JNK3 to which an I49T-substituted dockerin polypeptide is fused at the N-terminal; (C) the results of analysis of the interaction between the recombinant cohesin and the recombinant JNK3 of which an I49G-substituted dockerin polypeptide is fused at the N-terminal).

FIG. 7 shows the results of analysis of the interaction between a cohesin and diversely-mutated dockerins by a surface plasmon resonance method. The result for the addition of calcium ion is shown in parallel to that for a chelating agent ((A) the results of analysis of the interaction between the recombinant cohesin and the recombinant JNK3 of which an I49N-substituted dockerin polypeptide was fused at the N-terminal; (B) the results of analysis of the interaction between the recombinant cohesin and the recombinant JNK3 of which an I49S-substituted dockerin polypeptide is fused at the N-terminal; (C) the results of analysis of the interaction between the recombinant cohesin and the recombinant JNK3 of which an L16T/I49T-substituted dockerin polypeptide is fused at the N-terminal).

Figure 8:
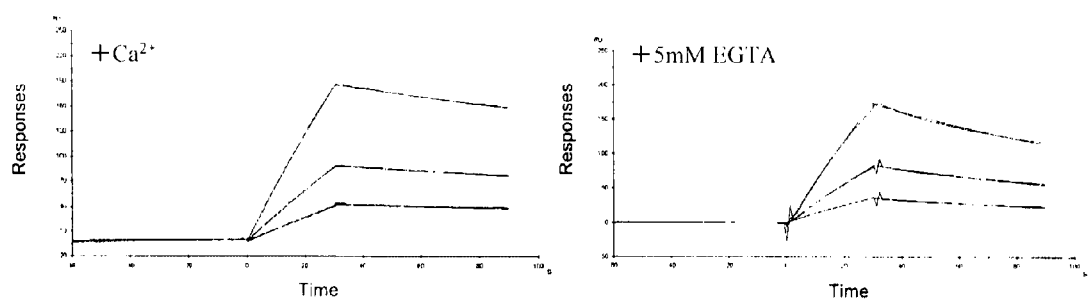

FIG. 8 shows the results of analysis of the interaction between a cohesin and diversely-mutated dockerins by a surface plasmon resonance method. The result for the addition of calcium ion is shown in parallel to that for a chelating agent (the results of analysis of the interaction between the recombinant cohesin and the recombinant JNK3 of which an I49V-substituted dockerin polypeptide is fused at the N-terminal).

The invention claimed is:

1. A recombinant dockerin polypeptide wherein the 14th amino acid isoleucine or leucine in the subdomain 2 of dockerin originating from *Clostridium josui* is substituted with an amino acid selected from the group consisting of threonine, glycine, serine, tyrosine and aspargine.

2. The recombinant dockerin polypeptide according to claim 1, wherein the 14th amino acid isoleucine or leucine in the subdomain 2 is substituted with threonine or glycine.

3. The recombinant dockerin polypeptide according to claim 1, comprising an amino acid sequence of SEQ ID NO: 4, SEQ ID NO: 5, SEQ ID NO: 6, SEQ ID NO: 7, or SEQ ID NO: 8.

4. A method for purification of a recombinant fused protein, the method comprising:
   binding a recombinant fused protein, comprising a target protein and the recombinant dockerin polypeptide according to claim 1, to a polypeptide comprising a cohesin domain via a calcium ion, to form a complex;
   removing the calcium ion from the complex by contacting the complex with a metal chelating agent; and
   eluting the recombinant fused protein.

5. The method for purification of a recombinant fused protein according to claim 4, wherein the polypeptide comprising a cohesin domain is immobilized on a carrier.

6. The recombinant dockerin polypeptide according to claim 1, wherein the 14th amino acid isoleucine or leucine in the subdomain 2 is substituted with threonine.

7. The recombinant dockerin polypeptide according to claim 1, wherein the 14th amino acid isoleucine or leucine in the subdomain 2 is substituted with glycine.

8. The recombinant dockerin polypeptide according to claim 1, wherein the 14th amino acid isoleucine or leucine in the subdomain 2 is substituted with serine.

9. The recombinant dockerin polypeptide according to claim 1, wherein the 14th amino acid isoleucine or leucine in the subdomain 2 is substituted with tyrosine.

10. The recombinant dockerin polypeptide according to claim 1, wherein the 14th amino acid isoleucine or leucine in the subdomain 2 is substituted with asparagine.

11. The recombinant dockerin polypeptide according to claim 1, wherein the 14th amino acid isoleucine or leucine in the subdomain 2 is substituted with threonine, and the 14th amino acid isoleucine or leucine in the subdomain 1 is substituted with threonine.

12. The recombinant dockerin polypeptide according to claim 1, wherein the 14th amino acid isoleucine or leucine in the subdomain 2 is substituted with glycine, and the 14th amino acid isoleucine or leucine in the subdomain 1 is substituted with glycine.

13. The recombinant dockerin polypeptide according to claim 1, comprising an amino acid sequence of SEQ ID NO: 5.

* * * * *